United States Patent
Norbeck et al.

(10) Patent No.: US 7,398,681 B2
(45) Date of Patent: Jul. 15, 2008

(54) GAS SENSOR BASED ON DYNAMIC THERMAL CONDUCTIVITY AND MOLECULAR VELOCITY

(75) Inventors: Joseph N. Norbeck, Riverside, CA (US); Chan Seung Park, Yorba Linda, CA (US); Michael Mc Clanahan, Riverside, CA (US); Colin E. Hackett, deceased, late of Riverside CA (US); by Nora Hackett, legal representative, Riverside, CA (US)

(73) Assignee: The Regents of the University of California, Oakland, CA (US)

( * ) Notice: Subject to any disclaimer, the term of this patent is extended or adjusted under 35 U.S.C. 154(b) by 149 days.

(21) Appl. No.: 11/234,511

(22) Filed: Sep. 22, 2005

(65) Prior Publication Data

US 2007/0169541 A1    Jul. 26, 2007

(51) Int. Cl.
*G01F 1/68* (2006.01)
(52) U.S. Cl. .................................................. 73/204.11
(58) Field of Classification Search ................ 73/25.03, 73/204.11; 382/187; 341/33; 345/174
See application file for complete search history.

(56) References Cited

U.S. PATENT DOCUMENTS

| | | | | | |
|---|---|---|---|---|---|
| 2,042,646 | A | * | 6/1936 | Willenborg | 436/149 |
| 3,167,956 | A | * | 2/1965 | Grey | 374/35 |
| 3,186,229 | A | * | 6/1965 | Liben | 73/755 |
| 3,616,677 | A | * | 11/1971 | Oppegaard | 73/23.21 |
| 4,404,846 | A | * | 9/1983 | Yamauchi et al. | 73/118.2 |
| 4,736,302 | A | * | 4/1988 | Kinugawa et al. | 701/103 |
| 5,356,819 | A | * | 10/1994 | Ritschel | 436/147 |
| 5,463,899 | A | * | 11/1995 | Zemel et al. | 73/195 |
| 5,644,068 | A | * | 7/1997 | Okamoto et al. | 73/23.32 |
| 6,169,965 | B1 | * | 1/2001 | Kubisiak et al. | 702/136 |
| 6,290,388 | B1 | * | 9/2001 | Saul et al. | 374/44 |

OTHER PUBLICATIONS

Pascal Tardy, Jean-Rene' Coulon, Claude Lucat, Francis Menil, "*Dynamic Thermal Conductivity Sensor for Gas Detection*", Elsevier B.V., Science Direct Sep. 4, 2003, 63-65.
Aifan Chen, Ruixian Luo, Thiam-Chye Tan, and Chung-Chiun Liu. "*A Thick-Film Calorimetric Sensor for Monitoring the Concentration of Combustible Gases*" Sensors and Actuators, 19 (1989) 237-248.

* cited by examiner

*Primary Examiner*—Michael Cygan
(74) *Attorney, Agent, or Firm*—Berliner & Associates

(57) ABSTRACT

An apparatus and method for gas detection. The apparatus comprises a) a sample chamber for holding a gas sample, b) a sealable vacuum port in fluid communication with the sample chamber, for evacuating the sample chamber, c) a sealable inlet port in fluid communication with the sample chamber, for introducing the gas sample into the evacuated sample chamber, and d) a thermal conductivity sensing element at least partly disposed within the sample chamber, for measuring the thermal conductivity of the gas sample. A gas sample released into the evacuated sample chamber requires a time interval to contact the thermal conductivity sensing element. The time interval is a measure of gas speed. Thermal conductivity and temperature of the gas sample are measured following determination of gas speed. By determining three parameters in a single sample of gas, different gas mixtures having similar thermal conductivities can be distinguished.

14 Claims, 6 Drawing Sheets

GAS SENSOR BASED ON DYNAMIC THERMAL CONDUCTIVITY AND MOLECULAR VELOCITY

BACKGROUND

1. Field of Invention

This invention relates generally to gas sensors and methods of detecting gases.

2. Related Art

Gas detection methods based on the thermal conductivity transport property have been widely used because such methods do not show significant selectivity toward a specific gas. Thermal conductivity is defined as the rate at which heat flows through an area of a body or material. Since thermal conductivity is a bulk property of gases, methods based on this property are considered to be near universal or non-specific gas detection methods.

Typically, the thermal conductivity of a gas is measured by heating a resistance element such as a hot wire filament or a thermistor, and contacting the heated element with a gas sample. The temperature of the resistance element is determined by the thermal conductivity of the gas sample, with a change in temperature reflected as a change in resistance of the resistance element. In this method, the resistance element behaves as a thermal conductivity sensing element.

Certain gases, such as helium and hydrogen, have thermal conductivities that are much greater than the thermal conductivity of air, while other gases, such as nitrogen, argon, carbon dioxide, carbon monoxide, ammonia and nitrogen have thermal conductivities that are less than or similar to that of air. A detector such as a gas chromatograph, which measures thermal conductivity of a gas typically uses a carrier gas of high thermal conductivity to detect a specimen gas of low thermal conductivity, or a carrier gas of low thermal conductivity to detect a specimen gas of high thermal conductivity. For example, helium is used as a carrier gas for nitrogen detection, and nitrogen or argon is used as a carrier gas for hydrogen detection. In other thermal conductivity detector applications, specific gas analysis based on thermal conductivity has been limited to either binary gas mixtures of known gas species, or hydrogen gas in a mix of gases having similar thermal conductivities significantly different from hydrogen. Because these methods measure only a single bulk parameter of a gas sample, different gas mixtures having similar thermal conductivities cannot be distinguished.

SUMMARY

The present invention provides a device and a method for gas analysis in which three parameters—velocity, thermal conductivity and temperature—can be measured for a single gas sample. By determining three parameters in a single sample of gas, different gas mixtures having similar thermal conductivities can be distinguished, and gas mixtures having more components than binary compositions can be analyzed. In particular embodiments, the velocity, thermal conductivity and temperature of a single gas sample can be determined under high pressure and high temperature conditions. Further, the detection of hydrogen gas can be accomplished with less interference from background gases than existing hydrogen gas analyzers.

A device in accordance with the present invention is a gas sensor that includes: a) a sample chamber for holding a gas sample; b) a sealable vacuum port in fluid communication with the sample chamber, for evacuating the sample chamber; c) a sealable inlet port in fluid communication with the sample chamber, for introducing the gas sample into the evacuated sample chamber; and d) a thermal conductivity sensing element at least partly disposed within the sample chamber, for measuring the thermal conductivity of the gas sample. The gas sample can comprise one or more gaseous components. In the device, the inlet port is positioned relative to the thermal conductivity sensing element such that movement of the gas sample from the inlet port to the sensing element takes an interval of time. This time interval is a measure of the velocity of the gas sample. Thus, movement of the gas sample from the inlet port to the sensing element provides a measure of gas sample speed. Unlike other gas sensors, the device of the present invention can be fabricated without wetted or exposed parts, which cannot withstand high temperature and high pressure conditions. As such, the device can be used over a broader range of temperatures and pressures compared to other gas sensors.

The present invention also provides a method of analyzing a gas. The method comprises: a) creating a vacuum in a sample chamber of a gas sensor assembly; b) releasing a gas sample into the evacuated sample chamber; c) determining the speed of the gas sample; and d) determining the thermal conductivity of the gas sample.

The novel features which are believed to be characteristic of the invention, both as to its organization and method of operation, together with further objects and advantages will be better understood from the following description when considered in connection with the accompanying figures. It is to be expressly understood, however, that each of the figures is provided for the purpose of illustration and description only and is not intended as a definition of the limits of the present invention.

DETAILED DESCRIPTION

Figure 1:
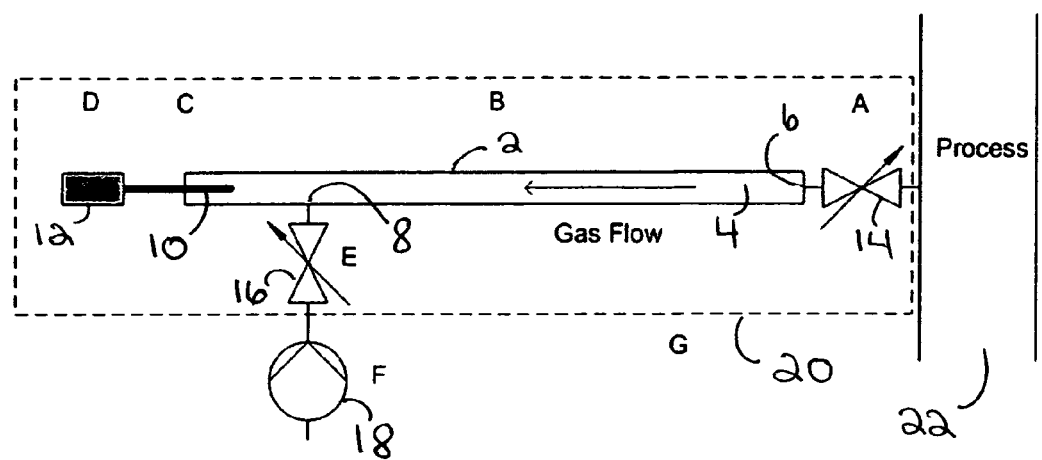
FIG. 1 is a schematic drawing of a gas sensor.

A schematic drawing of a sensor according to the present invention is shown in FIG. 1. The sensor comprises a sample vessel 2 having a sample chamber 4 in fluid communication with an inlet port 6 and a vacuum port 8. A thermal conductivity sensing element 10 is at least partially disposed in the sample chamber and is connected to a controller 12. A sample control valve 14, for controlling gas sample entry into the sample chamber, is connected to the inlet port 6. A vacuum control valve 16, for opening and closing the vacuum port 8, is connected at one end to the vacuum port 8 and at the other end to a source of vacuum 18. In this embodiment, the entire assembly, except for the vacuum source, is placed in a housing or sensor block 20, which can be fabricated from materials such as stainless steel, copper, brass, carbon steel and the like. However, as will be apparent to those skilled in the art, various parts of the gas sensor assembly can be separately located. For example, in other embodiments, the sample control valve, the vacuum control valve and/or the controller can be located externally to the sensor block. In FIG. 1, the gas sensor is shown connected to the flow 22 of a gas production process.

The sample chamber can be any size and shape so long as the speed and thermal conductivity of a gas sample can be measured. In preferred embodiments, the sample chamber is cylindrically shaped. Although the thermal conductivity sensing element can be at least partially disposed in the sample chamber, the thermal conductivity sensing element is preferably located entirely in the sample chamber.

The thermal conductivity sensing element can be any resistance device capable of detecting the thermal conductivity of a gas. The resistance device functions by providing heat and sensing temperature changes during the process of determining thermal conductivity. Examples of resistance devices include, but are not limited to, metal filaments, metal films, thermistors, hotplates, carbon films, carbon composites, metal wound wire, metal single wire and conductive plastics. The use and preparation of such resistance devices are well known in the art. For example, a thermistor is a thermally sensitive resistor having a positive or negative co-efficient of resistance. Thermistors having negative coefficients of resistance can be prepared from sensing materials such as manganese, nickel, copper, cobalt or other metallic oxides. Thermistors having a positive coefficients of resistance can be prepared from sensing materials such as barium titanate. Typically, thermistors are used at ambient or lower temperatures. Metal filaments can be made of sensing materials such as platinum, tungsten, rhenium-tungsten, nickel, nickel alloy, or gold-sheathed tungsten, and can be used at higher than ambient temperatures.

Figure 2:
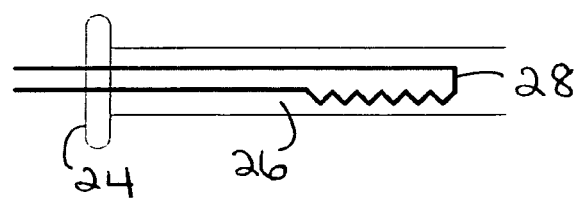
FIG. 2 is a schematic drawing of a filament and pressure seal.

Preferred embodiments of the gas sensor utilize a metal filament as the thermal conductivity sensing element. In some embodiments, the metal filament can be a typical filament used in gas chromatography detectors. FIG. 2 provides a schematic drawing of such a filament, and shows a pressure seal 24 attached to one end of a sample chamber 26, with an exposed filament 28 passing through the pressure seal and into the sample chamber. In other embodiments, the filament can be in the form of a bonded substrate sensor, such as prepared by thick or thin film deposition of a sensing material onto a ceramic or alumina plate.

The vacuum source can be any source known in the art, such as a vacuum pump, an aspirator or a house vacuum line.

The controller 12 regulates the amount of current flowing through the thermal conductivity sensing element. Preferably, the controller includes a Wheatstone bridge circuit, to regulate the resistance and voltage of the thermal conductivity sensing element. Other functions that the controller can perform are opening and closing the sample control and vacuum control valves, and regulating the operation of the vacuum source. The controller can also collect bridge output data, process the collected data, and calculate speed, thermal conductivity and temperature values. However, as is apparent to those skilled in the art, the additional functions can be performed by separate components of the sensor assembly.

The temperature of the sensor assembly can be maintained by a heating element incorporated into the sensor block and controlled by the controller 12 or by a separate temperature controller. In other embodiments, sensor temperature is maintained by placing the sensor assembly in an oven or incubator set at a desired temperature.

In accordance with the present invention, gas speed, thermal conductivity and gas temperature can be measured at gas pressures up to about 500 psia and at gas temperatures up to about 800° C. The gas pressure is preferably about 100 psia to 500 psia, more preferably about 200 psia to 500 psia, and even more preferably, about 300 psia to 500 psia. Gas temperature is preferably about 100° C. to 800° C., more preferably about 200° C. to 800° C., even more preferably about 250° C. to 800° C.

In operation, the current level through the thermal conductivity sensing element is set to above or at the self-heating point of the element, and the electrical resistance of the thermal conductivity sensing element is continuously monitored. The sample chamber 4 is evacuated to a selected negative pressure. This is accomplished by closing the sample control valve 14, opening the vacuum valve 16, and applying the vacuum source to create a vacuum within the sample chamber until a vacuum of about $2 \times 10^{-2}$ torr, for example, is achieved. The electrical resistance value of the thermal conductivity sensing element can be interpreted as being proportional to the absolute pressure or the degree of vacuum inside the sample chamber. Next, a gas sample is introduced into the evacuated sample chamber by momentarily opening the sample control valve. The speed of the gas sample is determined by measuring the time required for the gas sample to reach the thermal conductivity sensing element 10 after the sample control valve is opened. Contact of the gas sample with the thermal conductivity sensing element is indicated by a rapid change in electrical resistance of the sensing element. Gas speed is dependent on the molecular weight of the gas species present in the gas sample, and the absolute temperature of the gas. After the electrical resistance of the thermal conductivity sensing element reaches an equilibrium value, the thermal conductivity of the gas sample can be determined. Following the thermal conductivity measurement, the temperature of the gas sample is determined by lowering the current through the sensing element to below the self-heating point.

Figure 3:
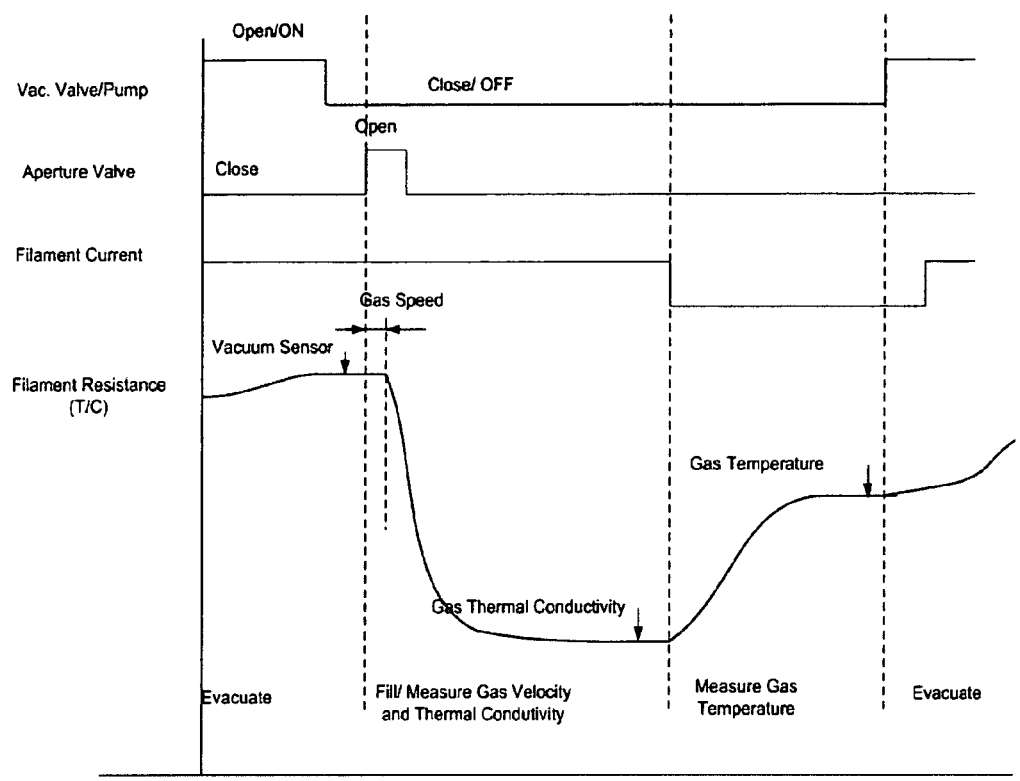
FIG. 3 is a diagrammatic representation of a single measurement cycle.

A single measurement cycle can be performed as shown diagrammatically in FIG. 3. For ease of description, the cycle is described by referring to the gas sensor shown in FIG. 1, where the thermal conductivity sensing element is a metal filament that is connected to a Wheatstone Bridge circuit. However, similar cycles can be performed with other embodiments of the gas sensor assembly. The cycle is divided into three steps: 1) chamber evacuation; 2) fill and capture speed and thermal data; and 3) temperature measurement. These events can be repeated for a continuous measurement process.

In the first step, bridge current is set to slightly heat the filament above the self-heating point with a known current, the aperture valve is closed, a vacuum pump is engaged, and the vacuum valve is opened to evacuate residual gases from the sample chamber. Bridge output is monitored until stable.

In the second step, the vacuum valve is closed, the aperture valve is opened, and sample gas is introduced. Bridge output data and gas speed timing data are collected, while the resistance signal reaches its equilibrium value.

In step three, the bridge current is lowered to below the self-heating point of the filament, and the temperature data is recorded. Once the activation current of the filament is reduced, the filament resistance reflects the gas temperature independent of gas composition.

The thermal conductivity can be calculated from the bulk resistance value using the measured gas temperature as a correction factor.

An oscilloscope can be used to capture bridge output values during a measurement cycle. Data can be processed using a commercial spreadsheet such as Excel (Microsoft Corporation, Richmond, Wash., USA). Alternatively, a purpose-built sensor can use a micro controller unit to read incoming data from the bridge circuit, detect initial slope, read the output signal in vacuum and the final output signal from the saturated chamber, then measure actual gas temperature, all in real time. The data captured during a measurement event can be stored in an array, and the micro controller software can calculate speed, the thermal conductivity data, and the final temperature data.

Figure 4:
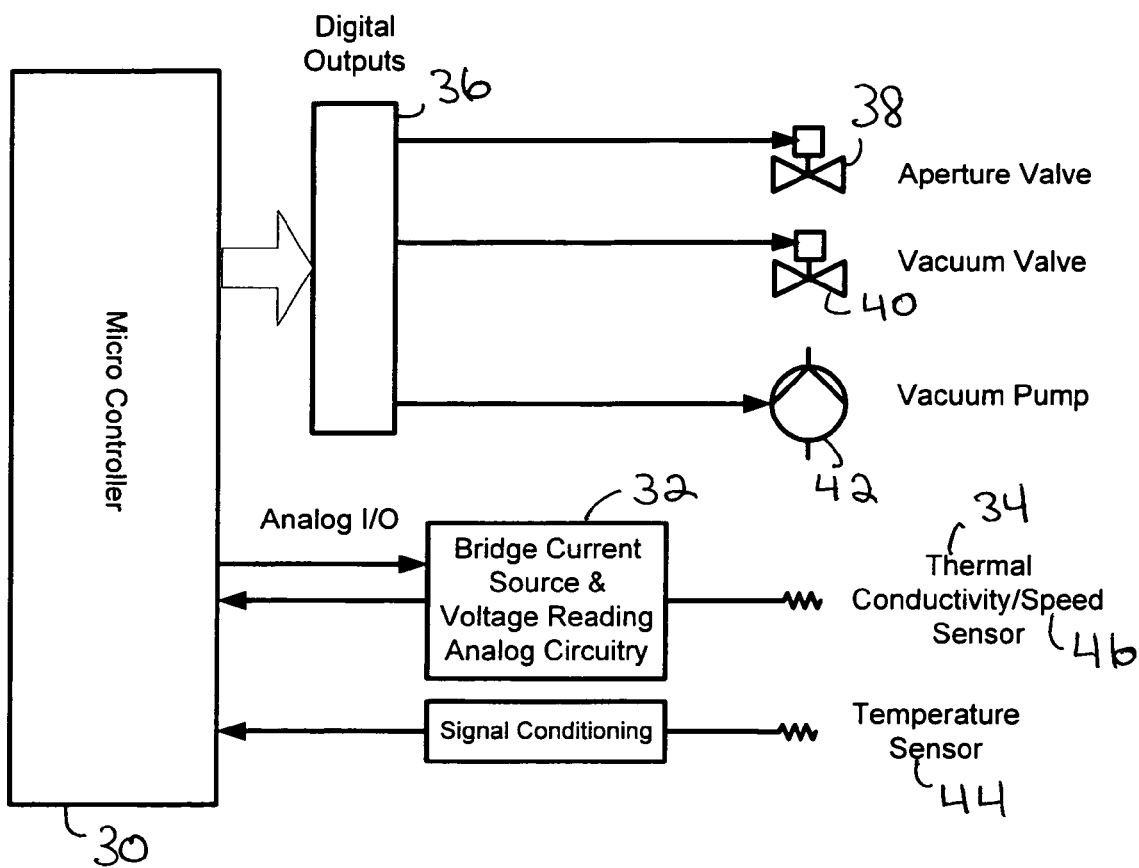
FIG. 4 is a block diagram of a gas sensor assembly.

FIG. 4 provides a block diagram of a sensor assembly according to the present invention. A micro controller 30 sends information to a bridge current source and receives a voltage reading from this analog circuit 32 electrically connected to a thermal conductivity sensing element 34. The micro controller sends command signals to the bridge current source to regulate bridge current and measures the voltage imbalance of the bridge caused by the changes in sensor resistance. The micro controller also controls signals from the digital outputs 36 that regulate the opening and closing of the aperture valve 38 and vacuum valve 40, and the operation of the vacuum pump 42.

The steps of measuring gas speed, thermal conductivity and temperature can be repeated on another gas sample to obtain a new set of data, and can be repeated continuously to provide close to real time analysis of gas mixtures.

In the embodiment shown in FIG. 1, the thermal conductivity sensing element has a resistance component, such as a filament that comprises ¼ of a Wheatstone bridge, that senses both thermal conductivity and temperature under two separate current regimes. In other embodiments, an independent temperature sensing component such as a conventional thermocouple or a resistance temperature detector ("RTD") could be added into the sample chamber. The addition of a separate temperature sensing component 44 is shown in FIG. 4.

Although a thermal conductivity sensing element can both detect the presence of a gas sample for the measurement of gas speed, and measure thermal conductivity of the gas sample, in other embodiments, the measurement of gas speed can be performed by a separate gas detecting element of the gas sensor assembly. The gas detecting element can be any gas detecting element capable of detecting the components of the gas sample, so long as the gas detecting element can be incorporated into a sample chamber. The gas sensor assembly in this case comprises: a) a sample chamber for holding a gas sample; b) a sealable vacuum port in fluid communication with the sample chamber, for evacuating the sample chamber; c) a sealable inlet port in fluid communication with the sample chamber, for introducing the gas sample into the evacuated sample chamber; d) a gas detecting device at least partially disposed in the sample chamber, for detecting the gas sample; and e) a thermal conductivity sensing element at least partly disposed within the sample chamber, for measuring the thermal conductivity of the gas sample. A gas detecting element is shown as a speed sensor 46 in FIG. 4.

Examples of gas detecting elements include, but are not limited to, infra-red sensors, electro-chemical sensors, and ceramic oxide based sensing devices such as those described in U.S. Pat. No. 5,439,580, incorporated herein by reference.

In further embodiments, the gas sensor of the present invention can be used to measure only gas speed independent of measuring thermal conductivity. The method of measuring gas speed alone comprises: a) creating a vacuum in a sample chamber of a gas sensor assembly; b) releasing a gas sample into the evacuated sample chamber; and c) determining gas speed by a method comprising measuring the interval of time necessary for the released gas sample to contact a thermal conductivity sensing element at least partially disposed in the sample chamber.

The present invention may be better understood by referring to the accompanying examples, which are intended for illustration purposes only and should not in any sense be construed as limiting the scope of the invention as defined in the claims appended hereto.

EXAMPLE 1

A gas sensor according to the present invention was constructed using a 0.25 inch O.D. stainless steel tube approximately 1 meter long, with Swagelok (Swagelok Company, Solon, Ohio, USA) or equivalent pressure fittings for the thermal conductivity sensing element, aperture valve, and vacuum valve connections. A tungsten-rhenium filament from GOW-MAC Instrument Co. (Bethlehem, Pa., USA) was employed as the thermal conductivity sensing element. Such a filament has a positive temperature coefficient that is linear along the temperature range from room temperature to 800° C. The filament was connected to the stainless steel tube by means of a pressure seal in an arrangement similar to that shown in FIG. 2. A Wheatstone bridge circuit was connected to the filament to monitor voltage changes in response to changes in filament resistance. The sensor block was maintained at 250° C. during sample measurements, a temperature that maintains water vapor and other condensable components in a gaseous state. To measure gas speed, thermal conductivity and gas temperature, a digital oscilloscope was used to capture the bridge output of the gas sensor. The data was post-processed using a commercially available program (Excel).

EXAMPLE 2

Measurement of Thermal Conductivity

Figure 5:
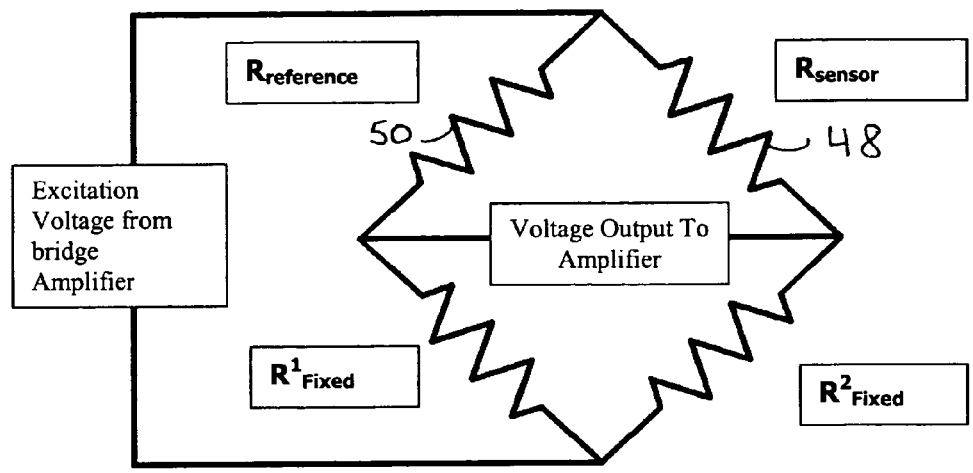
FIG. 5 is a drawing of a Wheatstone Bridge circuit incorporating a thermal conductivity sensing filament and a reference filament.

For a gas sensor constructed as in Example 1, the measurement of thermal conductivity relies on the fact that, when the current level through the metal filament is raised to or above the self-heating point of the filament, the resistance of the filament changes in proportion to the thermal conductivity of a gas sample that surrounds it. The equation defining the relationship between the thermal conductivity of the surrounding gas and the resistance of the filament is:

$$q = \frac{i^2 r}{J} \quad (1)$$

where q=rate of heat loss, i=current, r=resistance, and J=joules equivalent (4.19 w/cal). Referring to FIG. 5, when a metal filament 48 and a reference filament 50 are connected to a Wheatstone bridge circuit, and a constant-current source (i) applied, small changes in the filament resistance cause bridge voltage changes that can be accurately measured.

Figure 6:
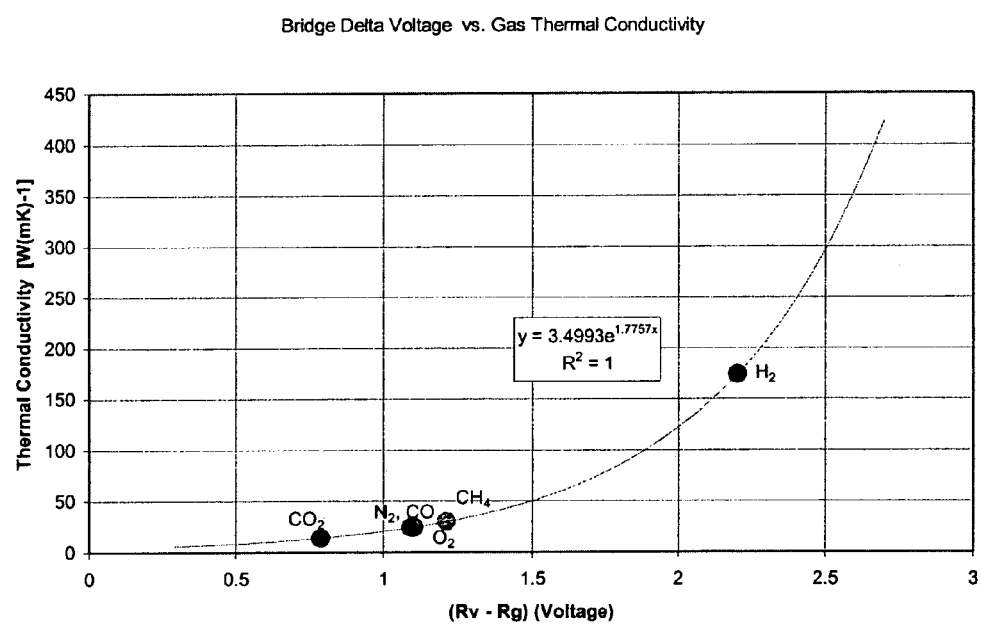
FIG. 6 is a graph of bridge delta voltage verse gas thermal conductivity.

At the start of each measurement cycle, a vacuum pump can be used to lower the pressure in the sample chamber, whereby the filament resistance approaches stability at $R_v$. Once vacuum is achieved, the vacuum valve can be closed to isolate the chamber, and the aperture valve opened. The sample gas then fills the sample chamber and the filament resistance reaches an equilibrium point, $R_g$, based on the thermal conductivity of the gas. The resulting difference ($R_v - R_g$) between this reading and the initial reading at vacuum is directly related to the thermal conductivity of the surrounding gas. FIG. 6 shows an example calibration curve of bridge delta voltage ($R_v-R_g$) verse gas thermal conductivity. Bridge delta voltage for $H_2$ and $CH_4$ were measured in actual experiments. Expected bridge delta voltage values for neat $N_2$, $CO_2$, CO and $O_2$ were derived using an exponential fit.

EXAMPLE 3

Measurement of Temperature

For a gas sensor constructed as in Example 1, the resistance of the filament is a direct indication of the absolute temperature of the surrounding gas when the current level of the filament is lowered to below the self-heating level of the filament. The electrical resistance of a filament at any temperature may be calculated by the following equation:

$$R_T = R_r[1+\alpha(T-T_r)] \quad (2)$$

where RT=conductor resistance at temperature T, $R_r$=conductor resistance at reference temperature $T_r$, and $\alpha$=temperature coefficient of resistance at the reference temperature $T_r$.

Figure 7:
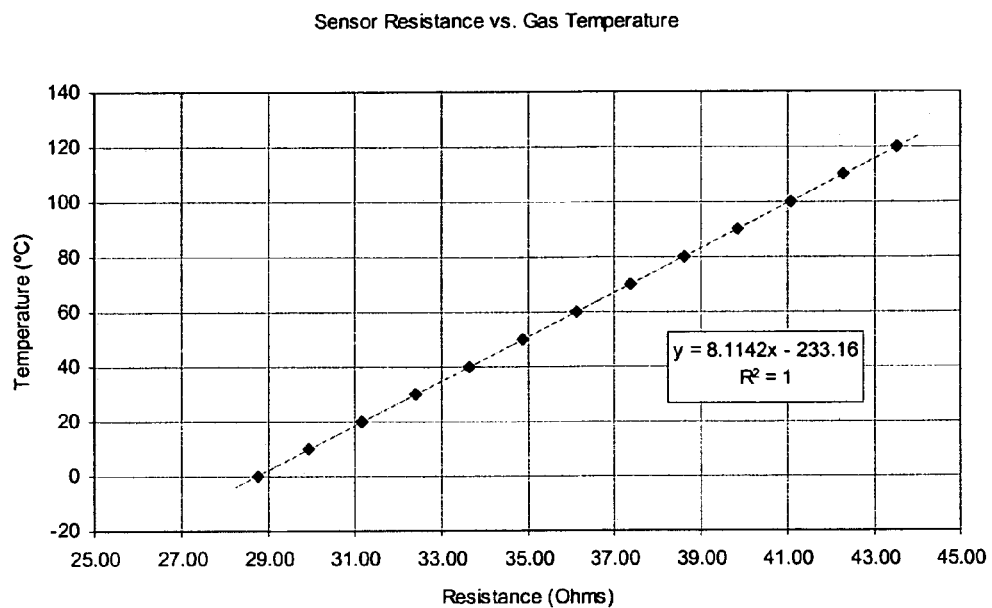
FIG. 7 is a graph of sensor resistance verse absolute temperature.

A gas sensor was constructed according to Example 1. The $\alpha$ value of the tungsten-rhenium filament was 0.00392 $\Omega$/cm-K ($T_r$=20° C.), and $R_r$ was 31.2 $\Omega$. FIG. 7 shows a calibration curve for the filament of the gas sensor.

EXAMPLE 4

Measurement of Gas Speed

For a gas sensor constructed according to Example 1, gas speed can be calculated by measuring the time difference (time delta) between the opening of the inlet valve and the sharp change of slope on the bridge circuit output that occurs when the thermal conductivity sensing element reacts as the first gas molecules begin to displace the vacuum. The faster the gas, the shorter the time delta will be. This time delta is a direct measurement of the speed ($v_{gas}$) of the fastest molecules in the sensor tube. The gas speed can be calculated from the following equation:

$$v_{gas} = \frac{(t_s - t_{vo})}{d} \quad (3)$$

where $t_s$=time of the detected change in slope of the bridge circuit, $t_{vo}$="valve open" command time or time zero, and d=is the distance between the valve opening and the sensor filament.

Figure 8:
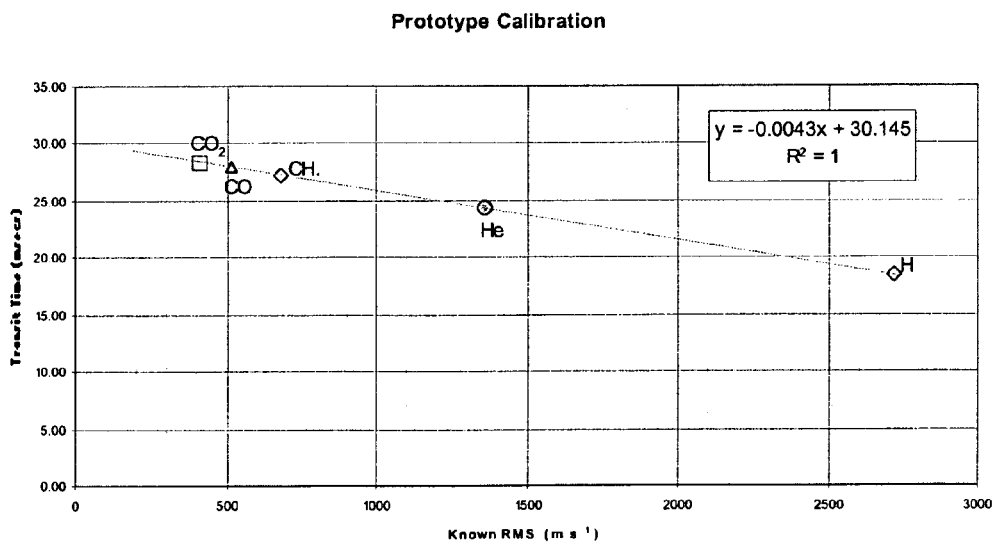
FIG. 8 is a graph showing gas speed of various gas samples.

For any given gas mixture and temperature, $v_{gas}$ will be constant. FIG. 8 shows a fit based in part on data collected from a gas sensor constructed according to Example 1. The gas speed for $H_2$ and $CH_4$ were measured in actual experiments. The measured $v_{gas}$ was plotted against published average speed of each species. Among the several different published values of average speed, Root Mean Square (RMS) value was chosen for this experiment. Expected speed values for neat He, CO and $CO_2$ are derived using a linear fit.

EXAMPLE 5

Gas Sample Measurement

Figure 9:
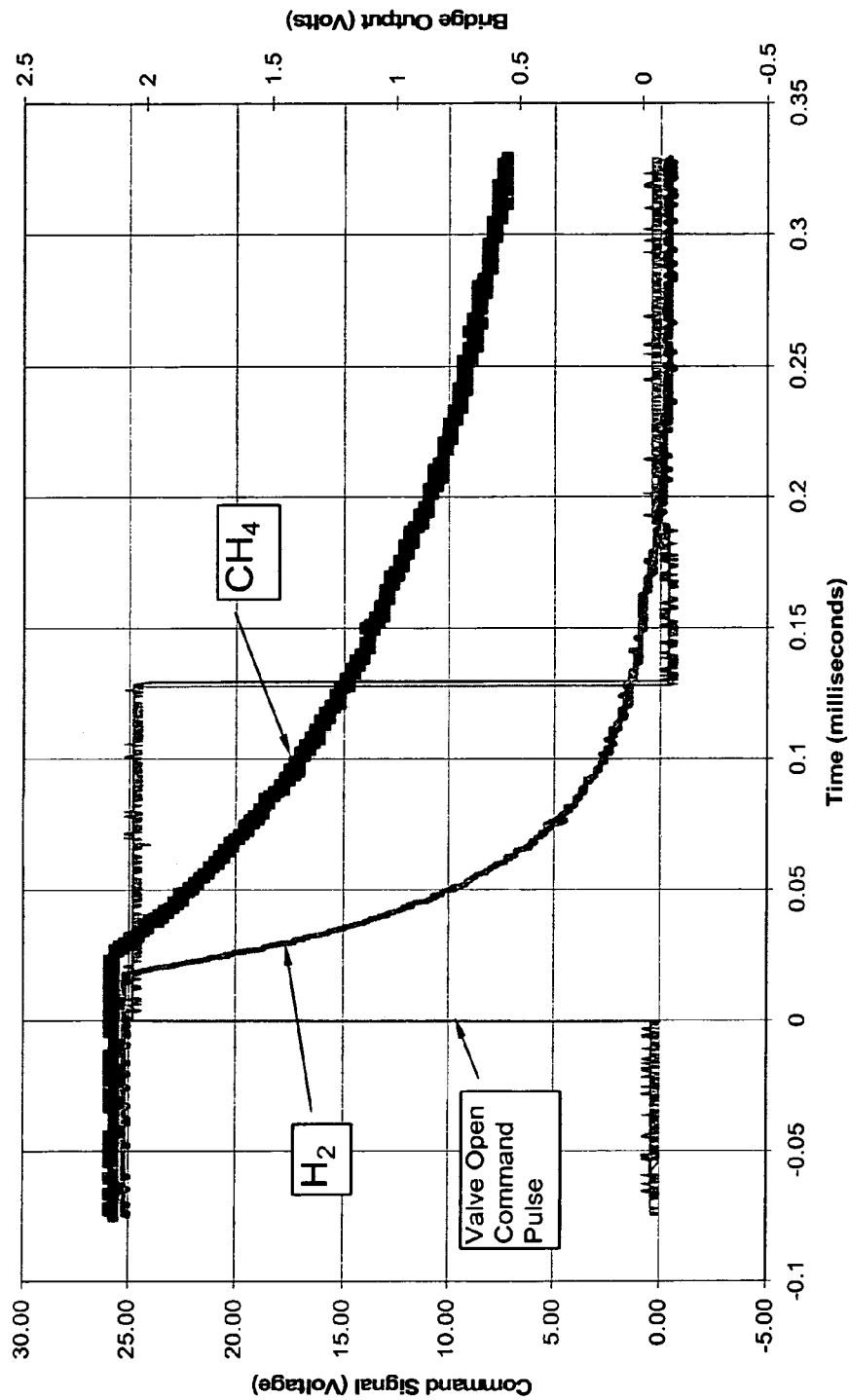
FIG. 9 is a graph showing voltage across a metal filament as a function of time.

A gas sensor was constructed as in Example 1. The thermal conductivity and gas speed of $H_2$ and $CH_4$ were determined. The results are shown in FIG. 9, which provides a graph of time verse voltage across the metal filament. Comparing the $H_2$ sample with the $CH_4$ sample, the time required for gas molecules to reach the filament from the inlet port increased as the molecular mass of the gas increased ($H_2$ to $CH_4$). In addition, the data show that the voltage across the filament at thermal equilibrium provides a measurement that is inversely proportional to the thermal conductivity of the gas.

EXAMPLE 6

Distinguishing Gas Samples on Basis of Gas Speed

The thermal conductivity and gas speed of two gas mixtures, 69% methane in nitrogen balance and 8% hydrogen in nitrogen balance, were calculated with commercially available software (Reaction Design, San Diego, Calif., USA). Table 1 lists the estimated thermal conductivity and average gas speed for each gas mixture. As shown, although the gas mixtures have approximately the same thermal conductivities, the gas mixtures can be distinguished on the basis of gas speed.

TABLE 1

| Gas Composition (mole 5) | Thermal Conductivity (erg/cm/K/s) | Average Gas Speed (@ 25° C., m/s) |
|---|---|---|
| 69% methane in nitrogen balance | 3.214E+03 | 488 |
| 8% hydrogen in nitrogen balance | 3.216E+03 | 1766 |

Although the present invention and its advantages have been described in detail, it should be understood that various changes, substitutions and alterations can be made herein without departing from the spirit and scope of the invention. Moreover, the scope of the present application is not intended to be limited to the particular embodiments of the process, manufacture, composition of matter, means, methods and/or steps described in the specification. As one of ordinary skill in the art will readily appreciate from the disclosure of the present invention, processes, manufacture, compositions of matter, means, methods, or steps, presently existing or later to be developed that perform substantially the same function or achieve substantially the same result as the corresponding embodiments described herein may be utilized according to the present invention. Accordingly, the invention is intended to include within its scope such processes, manufacture, compositions of matter, means, methods, or steps.

What is claimed is:

1. A gas sensor comprising:
   a sample chamber for holding a gas sample;
   a sealable vacuum port in fluid communication with the sample chamber, for evacuating said sample chamber;
   a sealable inlet port in fluid communication with the sample chamber, for introducing the gas sample into the evacuated sample chamber;
   a sample control valve connected to the inlet port, for controlling entry of the gas sample into the sample chamber; and
   a thermal conductivity sensing element at least partly disposed within the sample chamber spaced from the inlet port for measuring the thermal conductivity of the gas sample;
   a controller connected to the sample control valve to open the sample control valve and connected to the thermal conductivity sensing element for detecting a change in resistance of the thermal conductivity sensing element to detect initial reaction of the thermal conductivity sensing element to the gas sample, the controller determining the time from opening the sample control valve to initial reaction of the thermal conductivity sensing element to the gas sample to thereby provide a measure of the gas sample speed.

2. The gas sensor of claim 1, wherein the thermal conductivity sensing element is a metal filament.

3. The gas sensor of claim 1, further comprising a vacuum control valve connected to the vacuum port, for opening and closing said vacuum port.

4. The gas sensor of claim 1, further comprising a vacuum source connected to the vacuum port, for creating a vacuum within the sample chamber.

5. The gas sensor of claim 4, wherein the vacuum source is a vacuum pump, an aspirator or a house vacuum line.

6. The gas sensor of claim 1, wherein the controller includes a Wheatstone bridge circuit.

7. The gas sensor of claim 1, further comprising a temperature sensing element for measuring gas sample temperature.

8. A gas sensor assembly comprising:
- a cylindrical sample chamber having two ends, for holding a gas sample;
- a vacuum port in fluid communication with the sample chamber, for evacuating said sample chamber;
- an inlet port located at one end of the sample chamber and in fluid communication therewith, for introducing the gas sample into the evacuated sample chamber;
- a metal filament located at the other end of the sample chamber and at least partly disposed therein, for measuring thermal conductivity of the gas sample;
- a sample control valve connected to the inlet port, for controlling entry of the gas sample into the sample chamber;
- a vacuum control valve connected to the vacuum port, for opening and closing the vacuum port;
- a vacuum pump connected to the vacuum control valve, for creating a vacuum in the sample chamber; and
- a controller electrically connected to the metal filament, the control valves and the vacuum pump, for detecting a change in resistance of the metal filament on initial contact with the gas sample and for controlling the operation of the control valves and the vacuum pump, the controller determining the time from opening the sample control valve to initial reaction of the thermal conductivity sensing element to the gas sample to thereby provide a measure of the gas sample speed.

9. A method of analyzing a gas sample, the method comprising:
- creating a vacuum in a sample chamber of a gas sensor assembly;
- releasing a gas sample into the evacuated sample chamber at a first location in the chamber;
- determining when the gas sample is first released into the sample chamber
- at a second location spaced from the first location, determining when the thermal conductivity of the gas sample is first changed in response to the gas sample; and
- measuring a time interval for the released gas sample to travel from the first location to the second location to thereby provide a measure of the gas sample speed.

10. The method of claim 9, wherein the thermal conductivity determining step comprises measuring a change in resistance of a thermal conductivity sensing element in the presence of the gas sample.

11. The method of claim 10, wherein the thermal conductivity sensing element is a metal filament.

12. The method of claim 9, further comprising determining gas sample temperature.

13. The method of claim 9, wherein gas sample pressure is about 200 psia to 500 psia.

14. The method of claim 9, wherein gas sample temperature is about 250° C. to 800° C.

* * * * *